(12) United States Patent
Vaughn

(10) Patent No.: US 9,271,705 B2
(45) Date of Patent: Mar. 1, 2016

(54) SURGICAL INSTRUMENT ADAPTER WITH HIGHLY SECURE LOCKING SHAFT MECHANISM

(71) Applicant: Tyrone Vaughn, Kenosha, WI (US)

(72) Inventor: Tyrone Vaughn, Kenosha, WI (US)

( * ) Notice: Subject to any disclaimer, the term of this patent is extended or adjusted under 35 U.S.C. 154(b) by 166 days.

(21) Appl. No.: 13/915,955

(22) Filed: Jun. 12, 2013

(65) Prior Publication Data

US 2014/0371728 A1 Dec. 18, 2014

(51) Int. Cl.
*A61B 1/00* (2006.01)
*B23B 31/107* (2006.01)
*B23B 31/22* (2006.01)
*A61B 17/00* (2006.01)
*B23B 31/26* (2006.01)

(52) U.S. Cl.
CPC ....... *A61B 17/00234* (2013.01); *B23B 31/1071* (2013.01); *B23B 31/22* (2013.01); *B23B 31/263* (2013.01); *A61B 2017/00464* (2013.01); *A61B 2017/00477* (2013.01)

(58) Field of Classification Search
CPC A61B 1/00128; B23B 31/22; B23B 31/1071; B23B 31/263
USPC ........................... 606/1; 81/455, 459; 279/9.1
See application file for complete search history.

(56) References Cited

U.S. PATENT DOCUMENTS

| | | | | | |
|---|---|---|---|---|---|
| 2,990,188 | A | * | 6/1961 | Better et al. | 279/75 |
| 3,036,839 | A | * | 5/1962 | Williamson, Jr. | 279/24 |
| 3,684,302 | A | * | 8/1972 | Herman | 279/75 |
| 4,824,298 | A | * | 4/1989 | Lippacher et al. | 408/240 |
| 6,090,120 | A | * | 7/2000 | Wright et al. | 606/169 |
| 6,311,987 | B1 | * | 11/2001 | Rinne et al. | 279/4.03 |
| 6,966,730 | B1 | * | 11/2005 | Miyanaga | 408/204 |
| 2008/0244913 | A1 | * | 10/2008 | Lin | 30/167 |
| 2013/0078030 | A1 | * | 3/2013 | Simpson | 403/192 |

* cited by examiner

*Primary Examiner* — Lynsey Crandall
*Assistant Examiner* — Nathan J Jenness
(74) *Attorney, Agent, or Firm* — Absolute Technology Law Group, LLC

(57) ABSTRACT

A highly secure instrument adapter includes a handle with an internal locking and release mechanism which does not use a pushing release and which requires little physical effort to lock and release, yet provides a stable and secure connection between an instrument and the handle. The locking mechanism is comprised an ergometric handle having an open handle cavity, a receiver having an internal threaded tubular body and a plurality of locking apertures, and a rotating collar having a limited range of rotation, a plurality of fingers that project outward from the flattened surface on a spacer structure, and a plurality of circular apertures placed alternately between said fingers.

25 Claims, 15 Drawing Sheets

SURGICAL INSTRUMENT ADAPTER WITH HIGHLY SECURE LOCKING SHAFT MECHANISM

CROSS REFERENCE TO RELATED APPLICATIONS

This application claims priority to U.S. Provisional Application No. 61/659,889 filed on Jun. 14, 2012.

FIELD OF INVENTION

The present invention relates to the field of instrument adapters for attaching medical instruments to handles, and more specifically to a highly secure instrument adapter mechanism which allows a surgeon to quickly change an instrument shaft to alter the function of the instrument during a surgical procedure.

BACKGROUND

Figure 1:
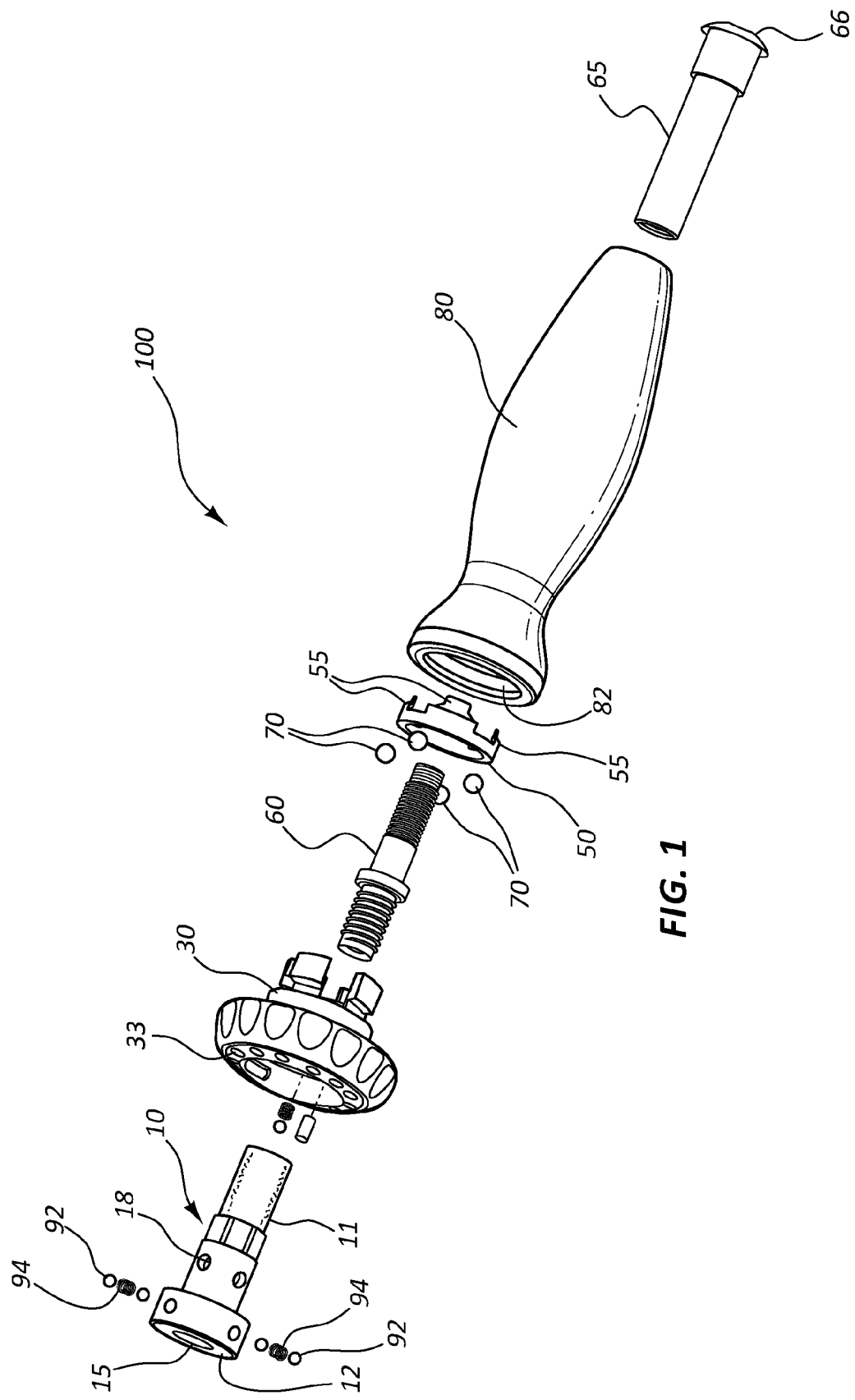
FIG. 1 is an exploded view of an exemplary secured instrument adapter mechanism.

Medical instrument handles utilize adapters to securely connect a variety of different instruments during surgical procedures. Most handles use adapters with locking and release mechanisms having intricate designs and multiple moving components. To prevent the locking and release mechanisms from damage and from exposure to bodily fluids and other debris, locking and release mechanisms are made interior to the handle.

Most internal release mechanisms use an external collar which is pushed inward towards the handle to release the shaft of an instrument. One limitation of these internal release mechanisms, however, is the stability of the external collar. When an external collar is bumped at a certain position with enough force, instruments are inadvertently released from the handle. A positive locking device would not cause an instrument to accidently release from the handle because of bumping or other vibrations.

Internal adapters known in the art also contain many components and moving parts which need to be manufactured separately and assembled. Additional parts mean additional manufacturing time and cost, as well as additional opportunities for parts to break and wear.

It is desirable to develop an internal release mechanism that does not use a pushing release.

It is desirable to develop an internal release mechanism that requires little physical effort to lock and release, yet provides a stable and secure connection between an instrument and the handle.

It is desirable to develop an internal release mechanism that uses positive, impact-proof locking.

TERMS OF ART

As used herein, the term "assembly" means a plurality of mechanical parts which may or may not operate interdependently to perform a mechanical function.

As used herein, the term "chamfer" refers to a beveled, angled or tapered edge which engages the edge of a second component to create a secured junction.

As used herein, the term "finger" means a flexible or non-rigid protruding structure.

As used herein, the term "inner contoured surface" refers to the inner surface of a finger which contains at least two distinctive sections having differing radii or angles.

As used herein, the term "interior receiver channel diameter" refers to the aperture in a sixty degree rotating collar which engages a receiver.

As used herein, the term "lead-in surface portion" refers to an initial portion of an inner contoured surface placed at an angle greater than that of a ramp surface portion.

As used herein, the term "locking engagement" refers to the portion of an inner contoured surface which is adapted to engage a ball bearing.

As used herein, the term "ramp surface portion" refers to a transitional portion of an inner contoured surface placed at an angle less than that of a lead-in surface portion.

SUMMARY OF THE INVENTION

The present invention is a highly secure instrument adapter with a rotating release rather than a pushing release. The device employs ball bearings and a small number of interlocking parts to achieve stability and positive, impact proof locking.

DETAILED DESCRIPTION OF INVENTION

For the purpose of promoting an understanding of the present invention, references are made in the text to exemplary embodiments of a secured instrument adapter mechanism, only some of which are described herein. It should be understood that no limitations on the scope of the invention are intended by describing these exemplary embodiments. One of ordinary skill in the art will readily appreciate that alternate but functionally equivalent structures and materials may be used. The inclusion of additional elements may be deemed readily apparent and obvious to one of ordinary skill in the art. Specific elements disclosed herein are not to be interpreted as limiting, but rather as a basis for the claims and as a representative basis for teaching one of ordinary skill in the art to employ the present invention.

It should be understood that the drawings are not necessarily to scale; instead, emphasis has been placed upon illustrating the principles of the invention. In addition, in the embodiments depicted herein, like reference numerals in the various drawings refer to identical or near identical structural elements.

Moreover, the terms "substantially" or "approximately" as used herein may be applied to modify any quantitative representation that could permissibly vary without resulting in a change in the basic function to which it is related.

FIG. 1 is an exploded view of an exemplary embodiment of a highly secure instrument adapter 100. As illustrated, highly secure instrument adapter 100 includes receiver 10, rotating collar 30, thrust washer 50, interconnect tube 60, handle core 65 that ends in cap 66, locking ball bearing 70, stabilizing ball bearings 92 and compression spring 94. Handle 80 secures receiver 10, rotating collar 30, thrust washer 50, interconnect tube 60, handle core 65 with cap 66, ball bearing 70, stabilizing ball bearings 92 and compression spring 94. In the exemplary embodiment shown, handle 80, with handle cavity 82, is illustrated as a simple handle designed to be easily grasped by one hand. However, in further exemplary embodiments, handle 80 may be any handle known in the art, including, but not limited to, torque-limiting handles.

Figure 2A:
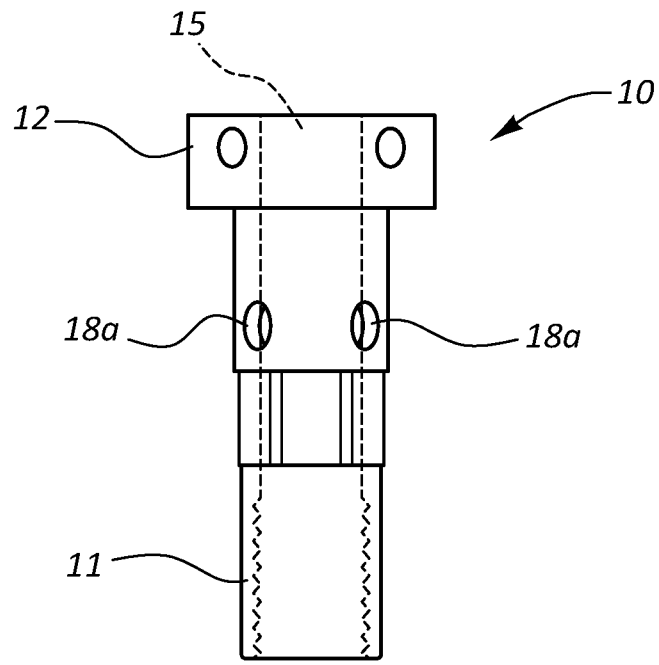
FIGS. 2a and 2b illustrate an exemplary receiver for a secured instrument adapter mechanism.
Figure 2B:
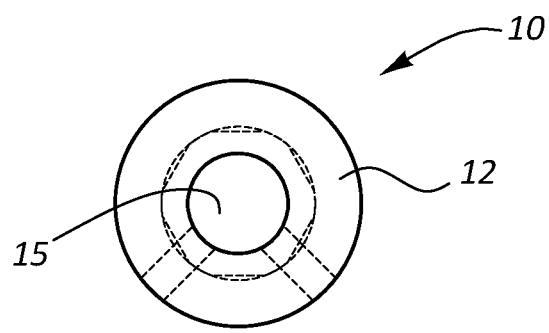

FIGS. 2a and 2b illustrate an exemplary receiver 10 in more detail. In the exemplary embodiment shown, receiver 10 is an internal threaded tubular body 11 with flat outside end surface 12 at the front of receiver 10 and centralized shaft cavity 15 creating a tubular passage completely through receiver 10. Receiver 10 is adapted to receive the shaft of a medical instrument so that the medical instrument shaft may slide within centralized shaft cavity 15.

Receiver 10 also includes four locking apertures 18a (18b, 18c and 18d not shown) approximately half way up internal threaded tubular body 11 from flat outside end surface 12. Locking apertures 18a (18b, 18c and 18d not shown) are configured to engage locking ball bearing 70 (not shown). In the exemplary embodiment shown, receiver 10 includes four equidistant and symmetrically arranged locking apertures 18a (18b, 18c and 18d not shown). However, in further exemplary embodiments, receiver may contain more or fewer locking apertures. In still further exemplary embodiments, locking apertures may not be equidistant from each other or may not be symmetrically arranged around internal threaded tubular body 11. In yet further exemplary embodiments, locking apertures 18a (18b, 18c and 18d not shown) may be at a different distance along internal threaded tubular body 11.

In the embodiment shown, receiver 10 also includes an additional stabilizing aperture (not shown) in the top end of internal threaded tubular body 11 near flat outside end surface 12 that is designed to house at least one stabilizing ball bearing 92 and compression spring 94.

Figure 3A:
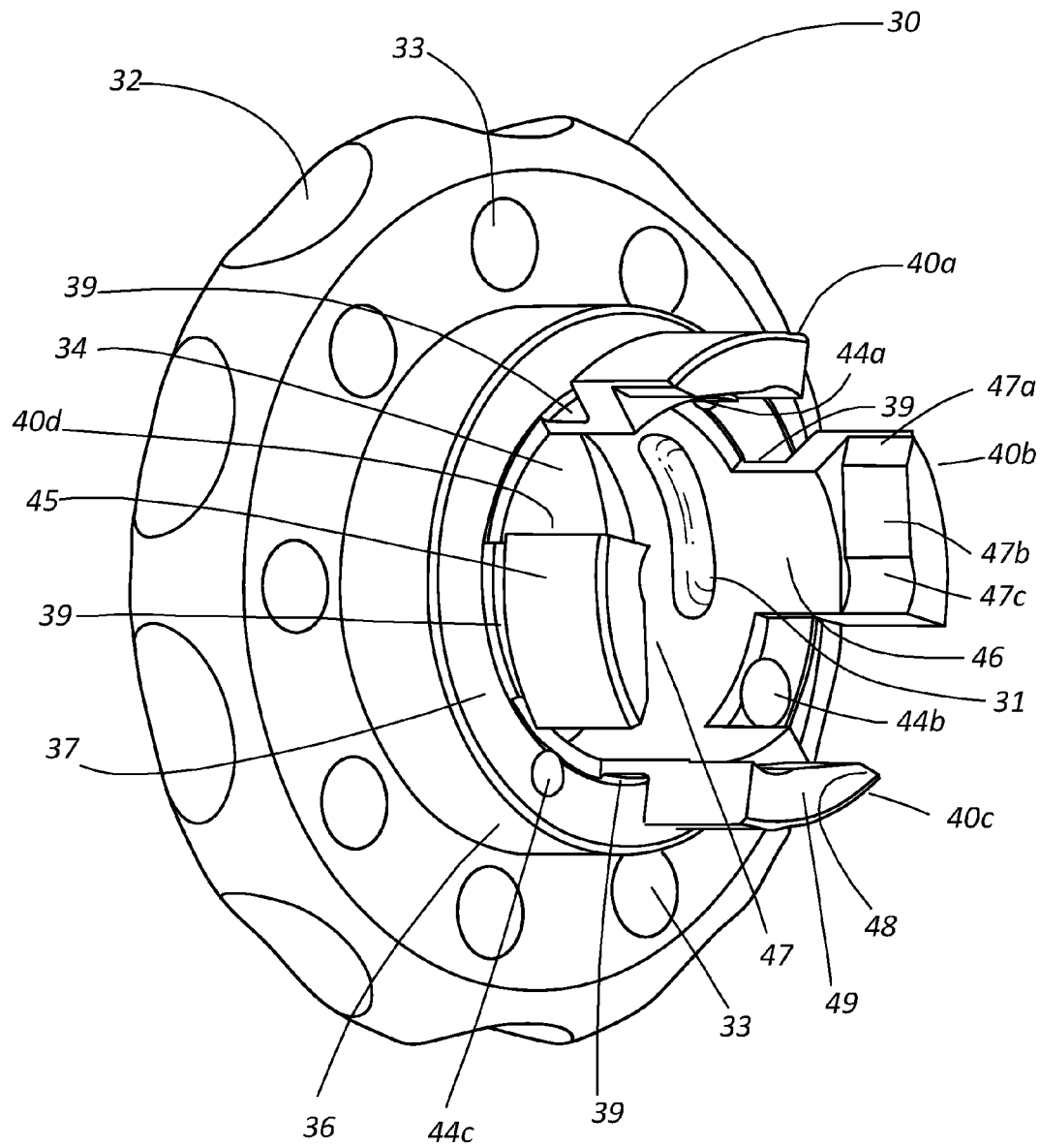
FIGS. 3a, 3b and 3c illustrate an exemplary sixty degree rotating collar for a secured instrument adapter mechanism.
Figure 3B:
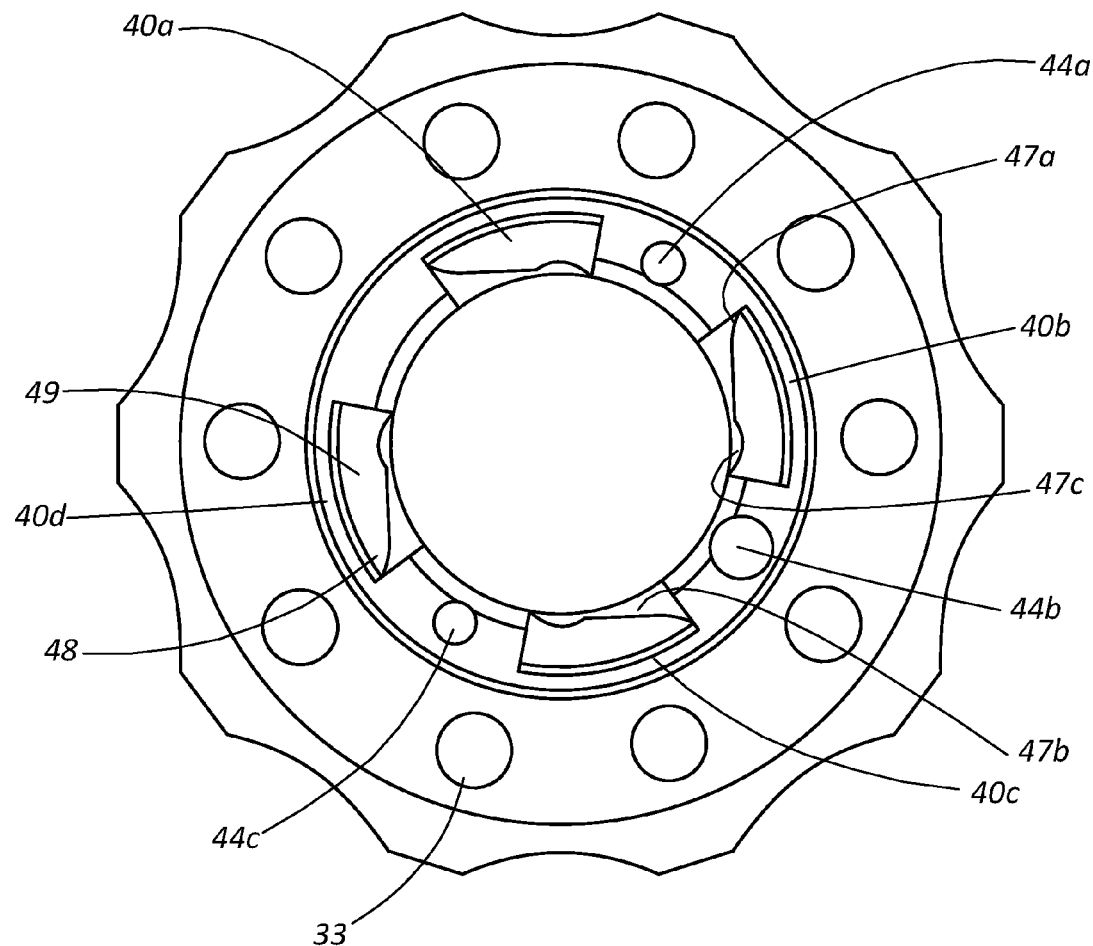
Figure 3C:
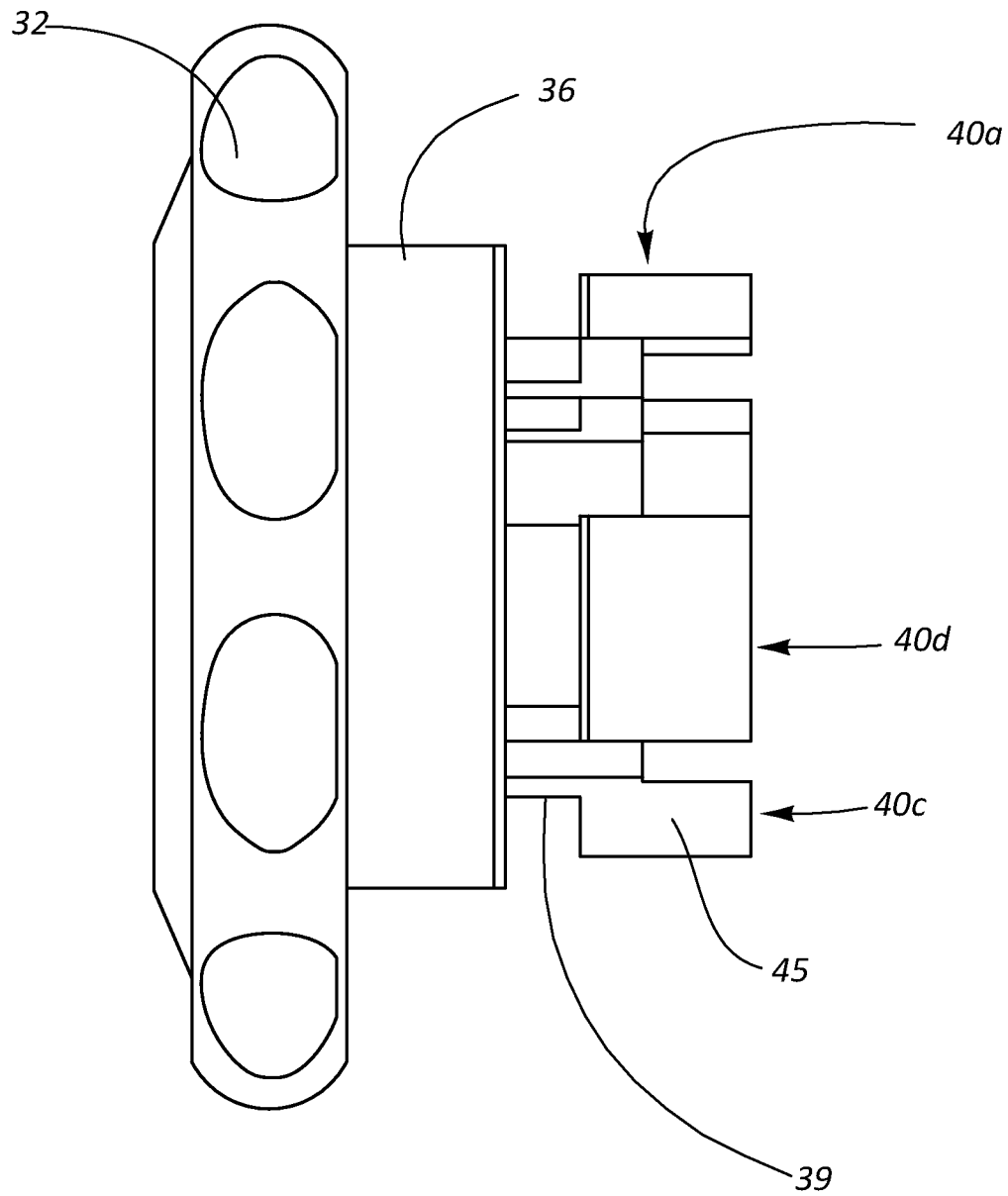

FIGS. 3a, 3b and 3c illustrate an exemplary rotating collar 30. FIG. 3a is a perspective view of rotating collar 30, illustrating radial frictional contours 32 around the perimeter of rotating collar 30. Rotating collar 30 includes at least one stabilizing ball bearing groove 31 that partially spans the inner surface of rotating collar 30. Receiver channel 34 runs the length of rotating collar 30 and has an internal diameter just larger than the external diameter of receiver 10 (not shown). In the exemplary embodiment shown, rotatable rotating collar 30 has an overall diameter just larger than the diameter for the front portion of handle 80 (not shown) near handle cavity 82 (not shown), so that handle 80 (not shown) is in contact with handle-contacting surface 38.

It is critical that one or more stabilizing design components and structures be utilized to ensure that instrument shaft 90 is stabilized and resistant to axial, transverse and angular movement during a surgical procedure.

In the exemplary embodiment shown, a stabilizing ball bearing assembly is utilized as the stabilizing component. In this exemplary embodiment, stabilizing ball bearings 92 and compression spring 94 exert a force to instrument shaft 90 when instrument shaft 90 is inserted into shaft cavity 15 and rotating collar 30 is rotated. When rotated collar 30 is rotated, a transverse force is applied to instrument shaft 90 by compressing compression spring 94 which engages a stabilizing ball bearing 92 against instrument shaft 90. Rotating collar 30 includes at least one stabilizing contoured ball bearing groove 31 that partially spans the inner surface of rotating collar 30. Stabilizing contoured ball bearing groove 31 is contoured so that it has a graduated variance in depth. Maximum force is applied to instrument shaft 90 when stabilizing ball bearing 92 is in contact with the shallowest portion of stabilizing contoured ball bearing groove 31.

In various embodiments, alternative stabilizing components such as springs, cams, contoured member, interlocking members, threaded components, protruberances and friction or pressure inducing members may be utilized to prevent movement of instrument shaft 90 during a surgical procedure. These alternatives may or may not be functionally equivalent to stabilizing ball bearing and spring assembly Also illustrated in FIG. 3a, on the inner surface of rotating collar 30, around receiver channel 34, rotating collar 30 includes an inward projection 36, which is designed to be in physical contact with the inner walls of handle cavity 82 (not shown) and terminates in flattened surface 37. In the exemplary embodiment shown, inward projection 36 creates receiver channel 34 having an interior diameter of 0.540 inches.

As illustrated in FIGS. 3a, 3b and 3c, rotating collar 30 also includes a plurality of fingers 40a, 40b, 40c, and 40d which project outward from flattened surface 37. In the exemplary embodiment shown, fingers 40a, 40b, 40c and 40d project 0.290 inches from flattened surface 37 and are 0.125 inches long. The length of fingers 40a, 40b, 40c and 40d however, may vary, as it is the radial measurement of contoured inner surface 47 portions which determine the exact length of fingers 40a, 40b, 40c and 40d.

As illustrated, spacer structure 39, a thinned down, flexible piece of material, holds fingers 40a, 40b, 40c and 40d a distance away from flattened surface 37. In the exemplary embodiment shown, spacer structure 39 is approximately 0.019 inches thick.

Alternating between fingers 40a and 40b, 40b and 40c, and 40c and 40d are circular apertures 44a, 44b and 44c, respectively. As illustrated in FIG. 3b, apertures 44a and 44c are identical and smaller than aperture 44b.

Looking specifically at fingers 40a, 40b, 40c and 40d, in the exemplary embodiments shown, each finger 40a, 40b, 40c and 40d has outer surface 45, which is curved at a consistent radius, and smooth inner surface 46, which is also curved at a consistent radius.

Approximately halfway along fingers 40a, 40b, 40c and 40d, however, smooth inner surface 46 transitions to inner contoured surface 47, which creates a tapered portion of fingers 40a, 40b, 40c and 40d with narrow end 48 gradually transitioning to wider end 49. As illustrated most visibly in FIG. 3b, contoured inner surface 47 of fingers 40a, 40b, 40c and 40d is not a consistent radius.

In the exemplary embodiments shown, contoured inner surface 47 consists of three distinct portions, each having a distinct critical angle or radius. First is lead-in surface portion 47a, near narrow end 48, which transitions to ramp surface portion 47b. Rample angle surface portion 47b is flatter.

Finally, locking engagement 47c, near wider end 49, is contoured to the radius of locking ball bearing 70 (not shown).

In further exemplary embodiments, rotating collar 30 may contain more or fewer fingers, and fingers may be differently spaced around flattened surface 37. In still further exemplary embodiments, fingers may be different dimesions, and the radii of contoured inner surfaces may differ to correspond to variations in receiver 10 (not shown) diameter or receiver channel 34 diameter.

However, it is desirable to have as few parts and components as possible for manufacturing, while still maintaining the desired locking and securing properties. Four fingers strikes an appropriate balance between complexity in manufacturing and functionality.

Figure 3D:
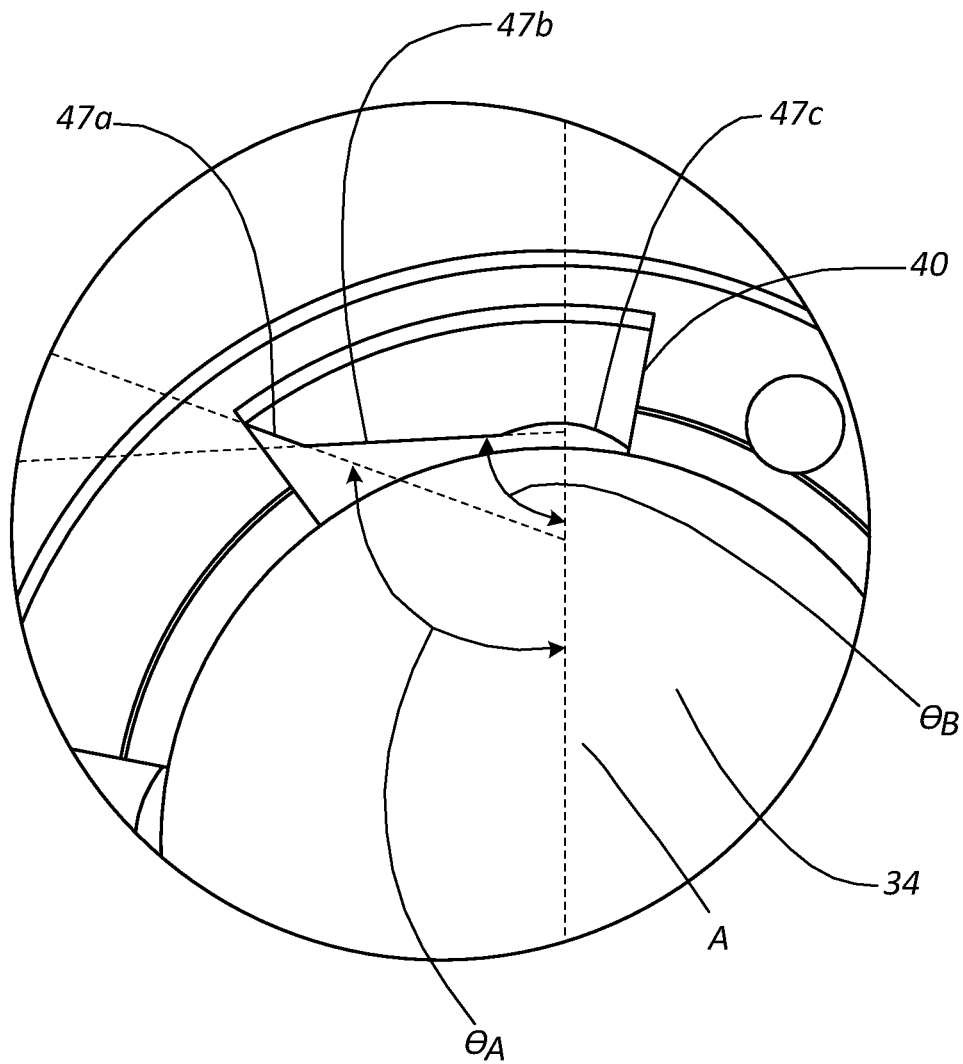
FIGS. 3d and 3e illustrate critical angles and measurements of the fingers.
Figure 3E:
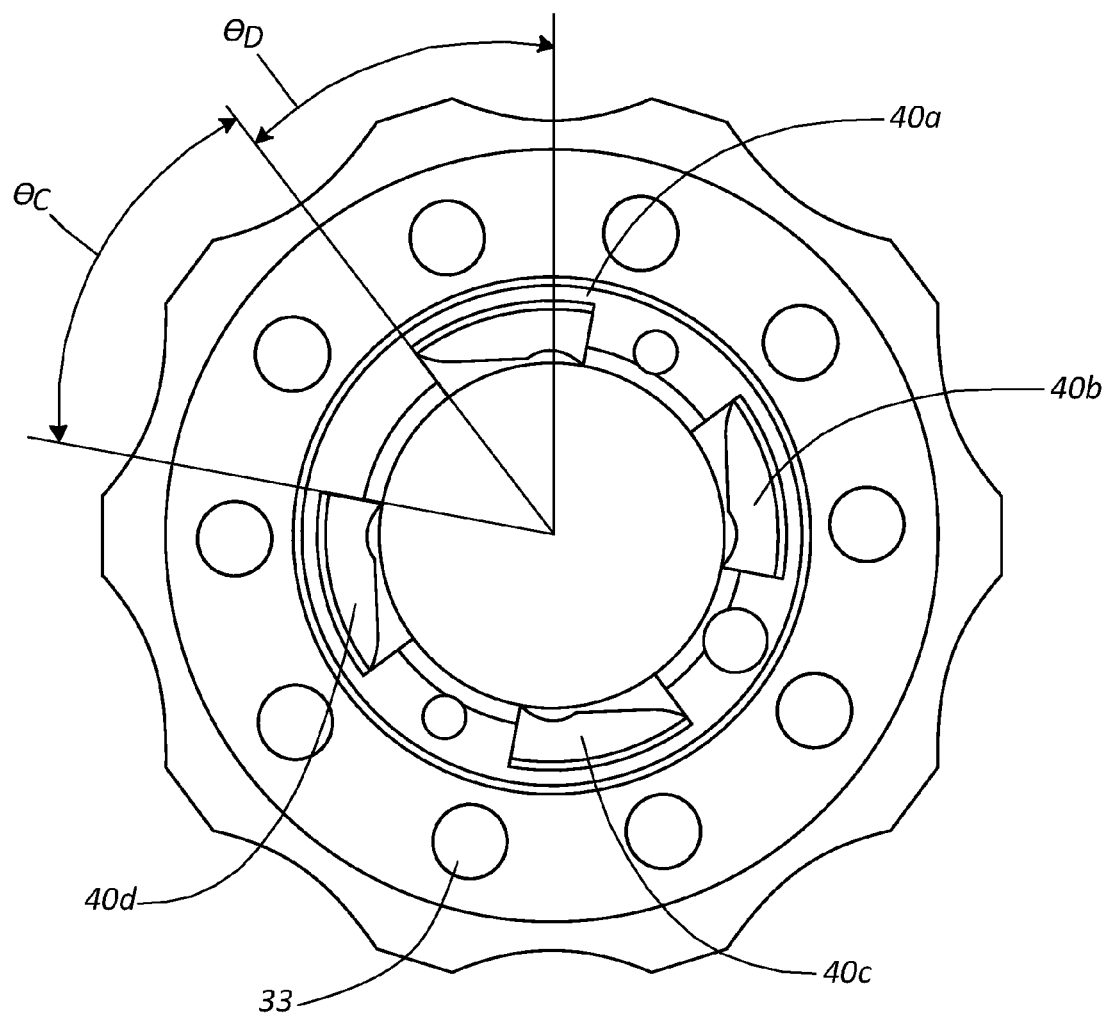

FIGS. 3d and 3e illustrate the critical angles and measurements of fingers 40. Lead-in surface portion 47a is placed at an angle of approximately 109.114 degrees as measured from the centerline A of receiver channel 34. This angle is illustrated as $\theta_A$ in FIG. 3d. Ramp surface portion 47b is placed at an angle of 86.502 degrees as measured from the centerline A of receiver channel 34. This angle is illustrated as $\theta_B$ in FIG. 3d.

Locking engagement 47c has a radius of 0.070, which is also the radius of locking ball bearing 70 (not shown). In order to securely and stably engage, locking engagement 47c and locking ball bearing 70 (not shown) must have corresponding radii.

In further exemplary embodiments, the exact angles of lead-in surface portion 47a and ramp surface portion 47b, as well as the radius of locking engagement 47c, may vary slightly. For example, the angle of ramp surface portion 47b is 86.052 degrees, but may vary by plus or minus 20 degrees. This allows for gradual engement of a instrument shaft and an increase in pressure on the specific finger 40 which is touching a locking ball bearing 70 (not shown). The angle of lead-in surface portion 47a may similarly vary by plus or minus 20 degrees. However, the exact radial measurement for locking engagement 47c may vary within an amount determined by the diameter and shape of locking ball bearing 70 (not shown), as the two radii must properly correspond to provide secure and stable engagement.

As illustrated in FIG. 3e, there is a distance of approximately 42.642 degrees, illustrated as $\theta_C$, between each finger 40a, 40b, 40c and 40d, with each finger 40a, 40b, 40c and 40d being approximately 47.358 degrees in ramp and engagement length. Further, finger 40a is shifted approximately 10.679 degrees from center, such that 36.679 degrees ($\theta_D$) of finger 40a occurs counterclockwise from 0 degrees. As illustrated in FIG. 3b, each subsequent finger 40b, 40c, 40d is shifted approximately 10.670 degrees from 90 degrees, 180 degrees, and 270 degrees, respectively, to be equally spaced along flattened surface 37.

In still further exemplary embodiments, fingers 40a, 40b, 40c and 40d may be separated by between 20 and 70 radial degrees, depending on the number and size of fingers required or desired. For example, some exemplary embodiments may use between 2 and 8 fingers; the more fingers, the closer together fingers will be.

Figure 4:
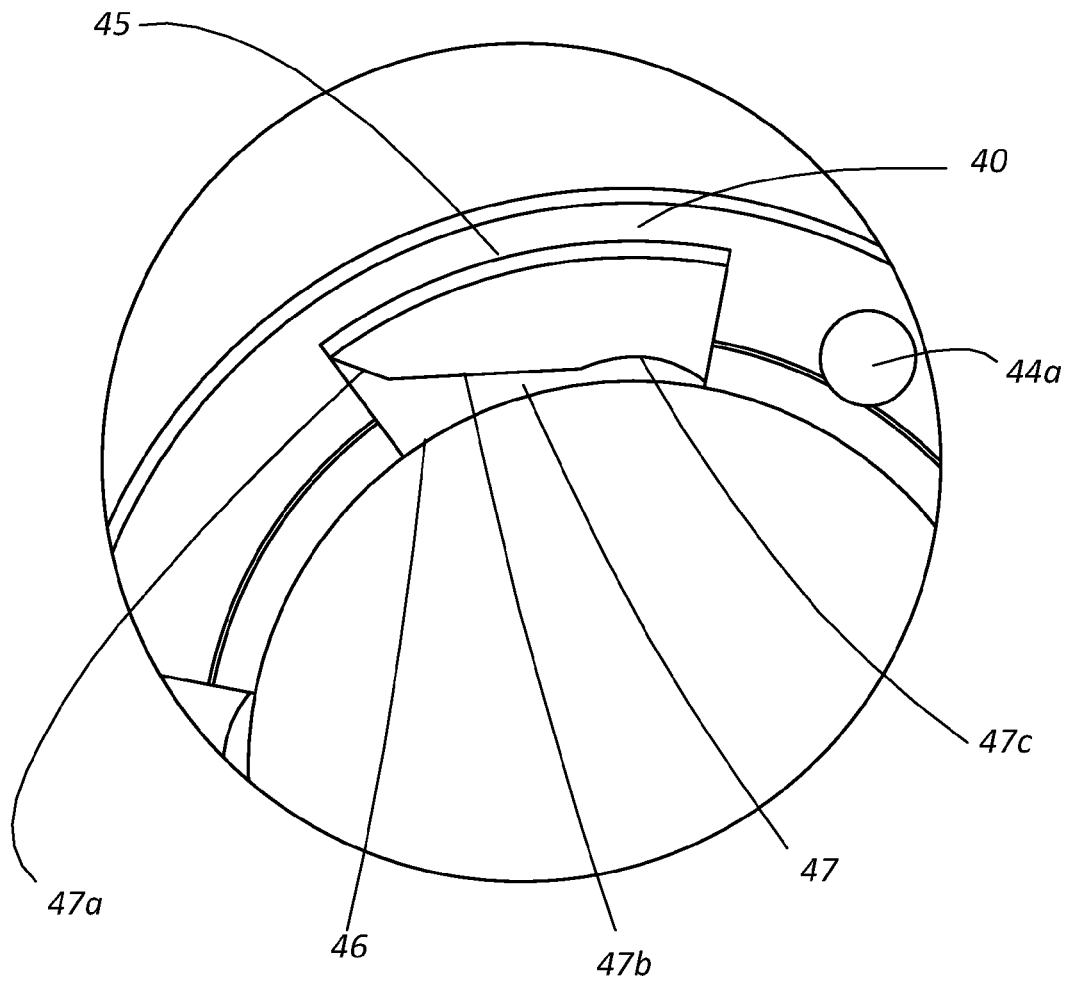
FIG. 4 illustrates an exemplary finger for a rotatable sixty degree rotating collar.

FIG. 4 illustrates an exemplary finger 40 in further detail. Finger 40 has outer surface 45 and smooth inner surface 46, each having a consistent radius corresponding to the inner and outer radii of outward projection 36 (not shown). Contoured inner surface 47 creates a tapered finger with a narrow end 48 and wider end 49 with its inconsistent radius. As illustrated, contoured inner surface 47 is divided into three sections, each having a different radius. Lead-in surface portion 47a has a larger radius, resulting in a steep ramp, while ramp surface portion 47b has a smaller radius, resulting in a flatter portion. Locking engagement 47c has a radius corresponding to that of locking ball bearing 70 (not shown).

Figure 5A:
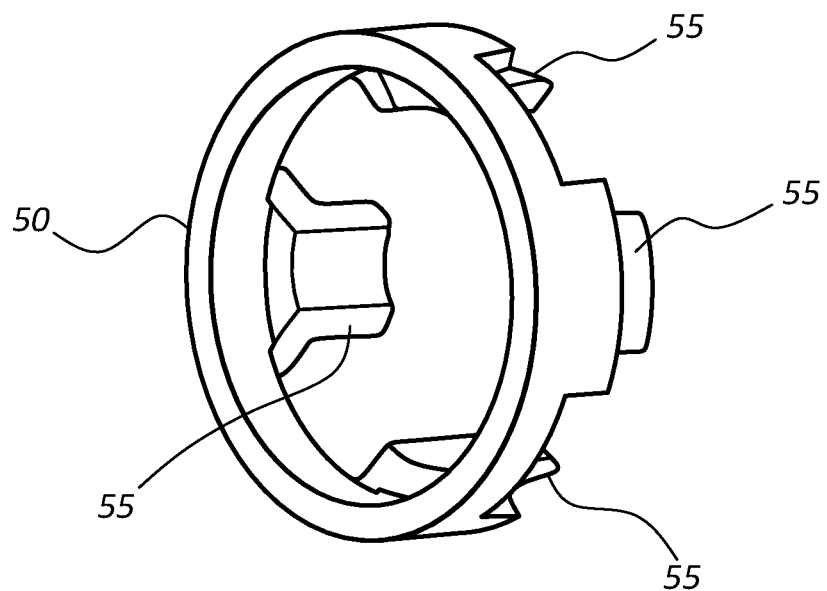
FIGS. 5a and 5b illustrate perspective and side views, respectively, of an exemplary thrust washer.
Figure 5B:
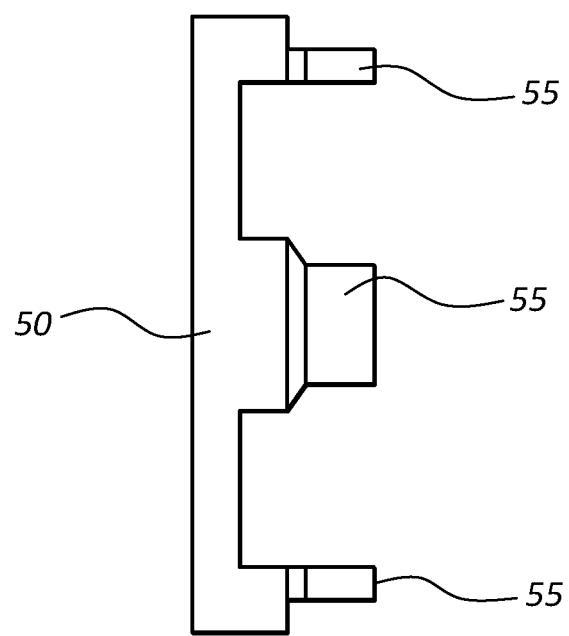

FIGS. 5a and 5b illustrate perspective and side views, respectively, of an exemplary thrust washer 50.

Figure 6:
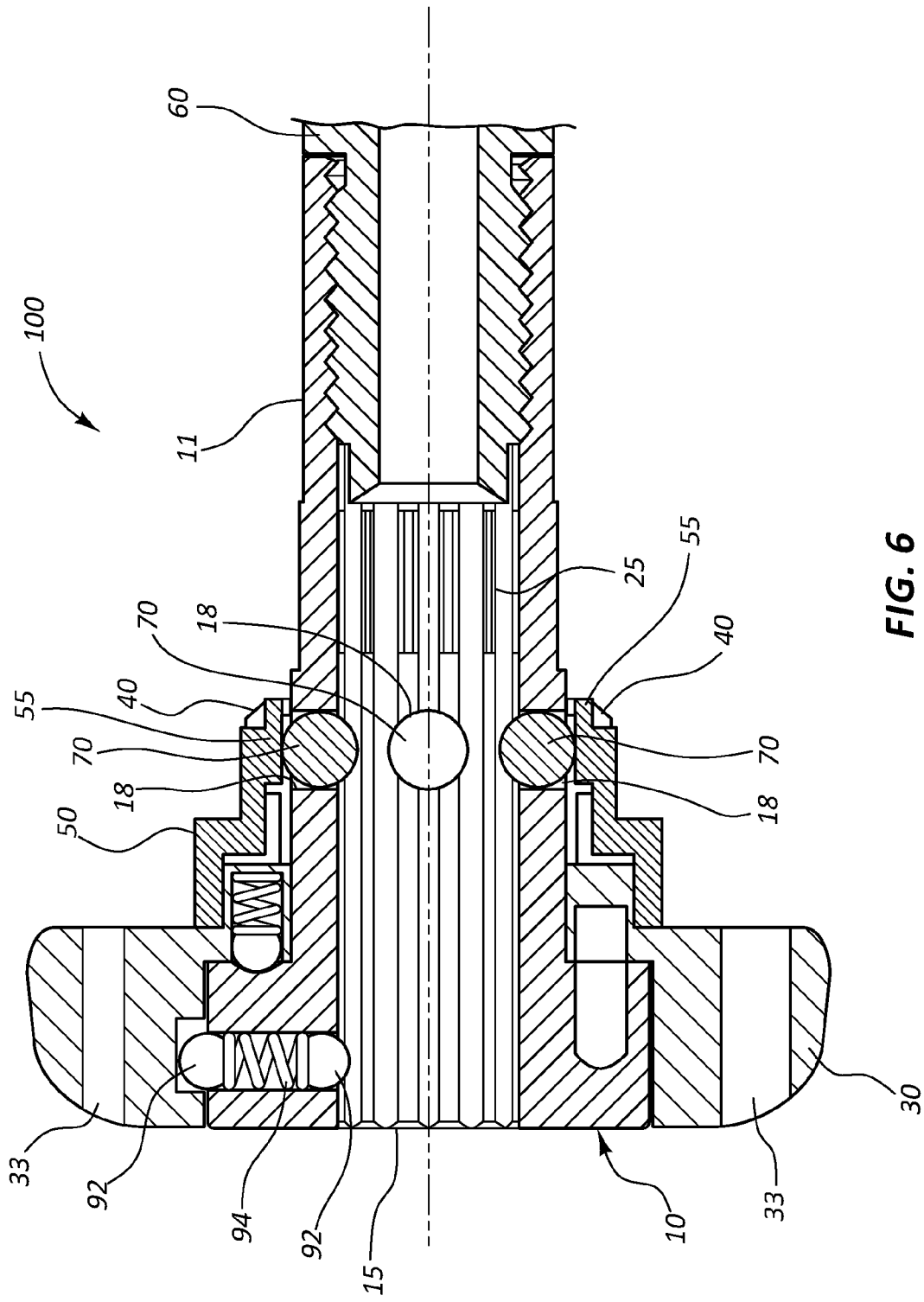
FIG. 6 illustrates an exemplary secured instrument adapter mechanism.

FIG. 6 illustrates an exemplary highly secure instrument adapter 100 fully assembled without an instrument shaft. Receiver 10 is in receiver channel 34 (not shown) of rotating collar 30, with internal threaded tubular body 11 adapted to engage threads on the exterior of interconnect tube 60. Fingers 40 correspond to apertures 18 of receiver 10, and thrust washer 50 is secured against the inner surfaces of fingers 40. Both ends of interconnect tube 60 contain exterior threads, with the anterior end of interconnect tube 60 attaching to internal threaded tubular body 11, and the posterior end of interconnect tube 60 attaching to handle core 65 (not shown) inside handle cavity 82 (not shown). Handle core 65 slides into handle cavity 82 from the posterior end of handle 80 (not shown) and is secured to handle 80 by its connection to interconnect tube 60 within handle cavity 82. The posterior end of handle core 65 widens to form a cap 66 (not shown) that fits against the posterior end of handle 80 and covers the posterior end of handle cavity 82.

Also illustrated in FIG. 6 are the internal contours of shaft cavity 15. Just inward from apertures 18 in the exemplary embodiment shown, centralizing chamfers 25 are triple square. However, in further exemplary embodiments, centralizing chamfers 25 may be any configuration, such as double square or hexagonal, to correspond to a particular instrument shaft. Interconnect tube 60 fits within end cavity 28 (not shown) of receiver 10.

Figure 7:
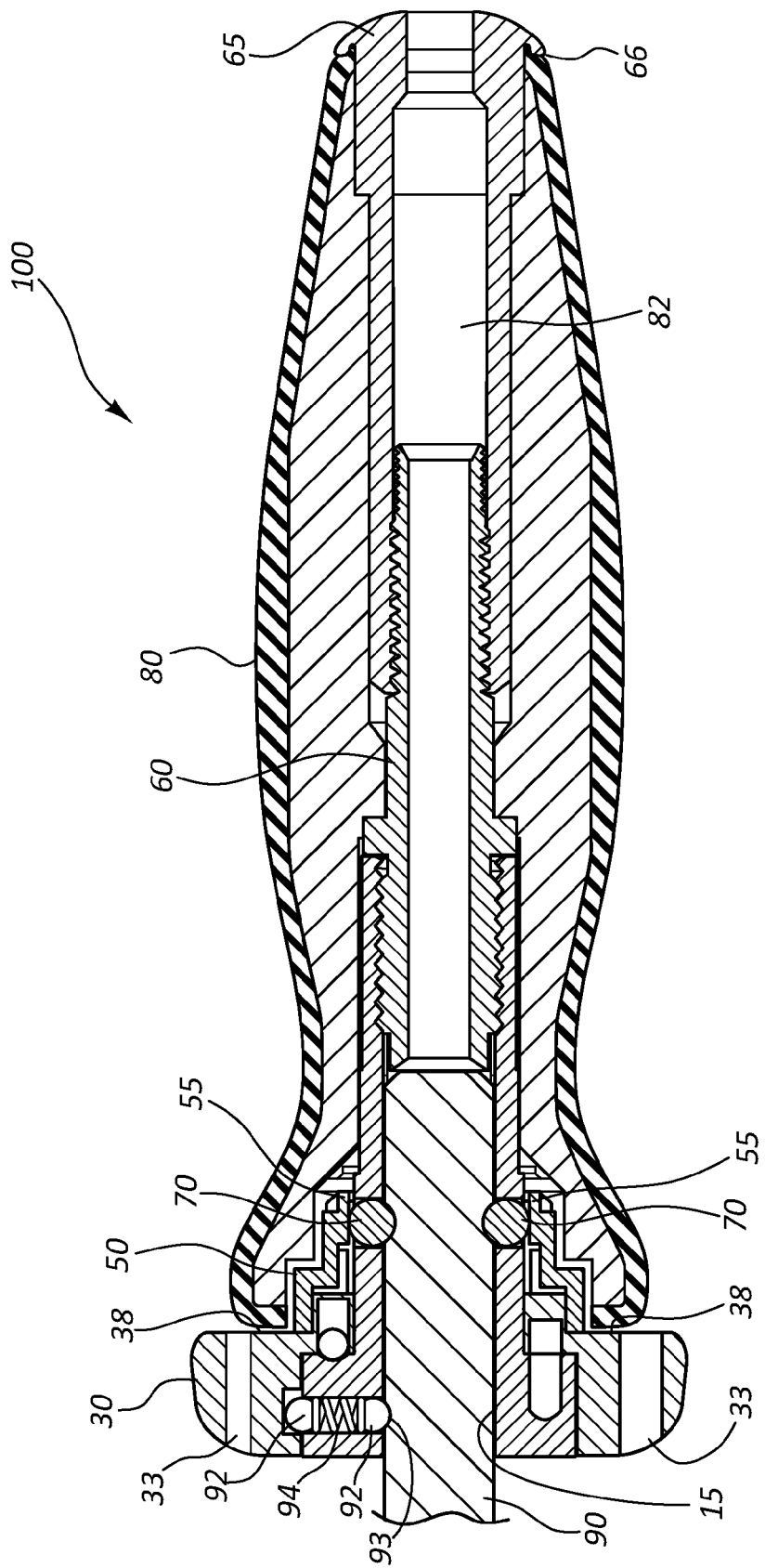
FIG. 7 illustrates an exemplary secured instrument adapter mechanism with an instrument shaft inserted in the adapter.

FIG. 7 illustrates an exemplary highly secure instrument adapter 100 with instrument shaft 90 inserted and secured in shaft cavity 15. As illustrated, instrument shaft 90 contains groove 93 which runs the circumference of instrument shaft 90 and engages stabilizing ball bearing 92.

Figure 8A:
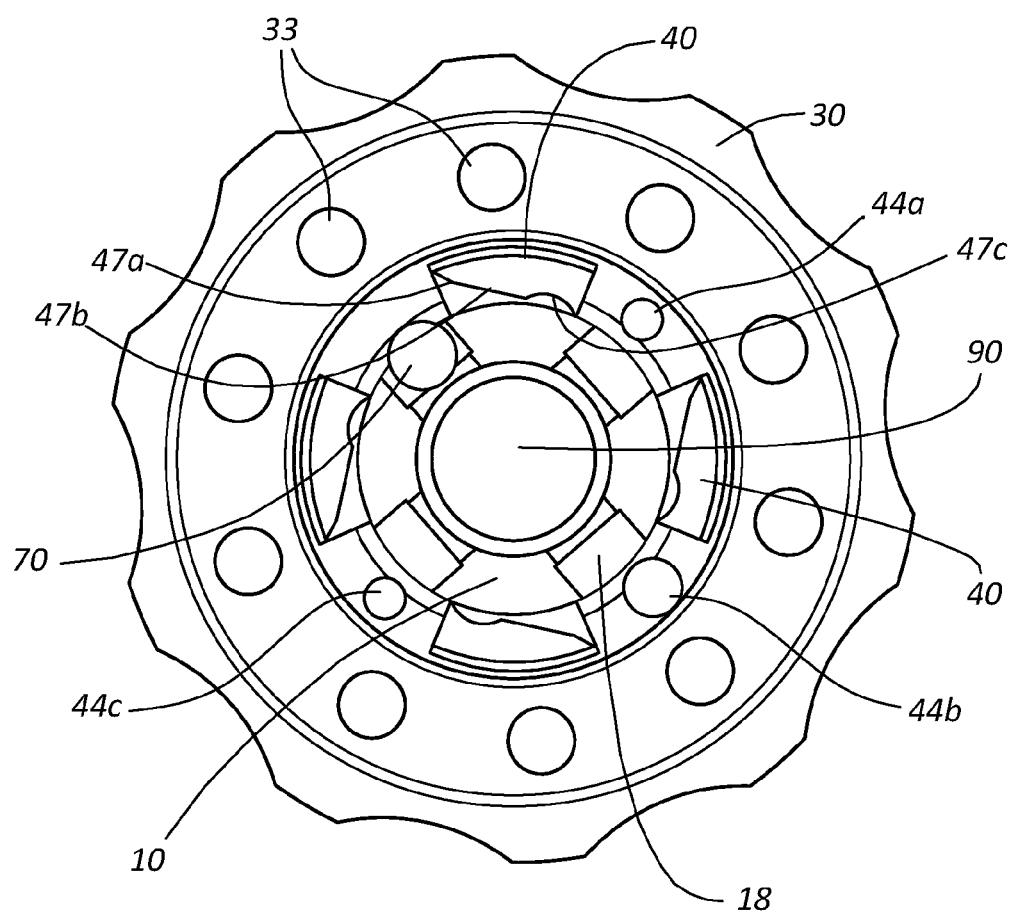
FIG. 8a illustrates an exemplary secured instrument adapter mechanism in its unlocked position.
Figure 8B:
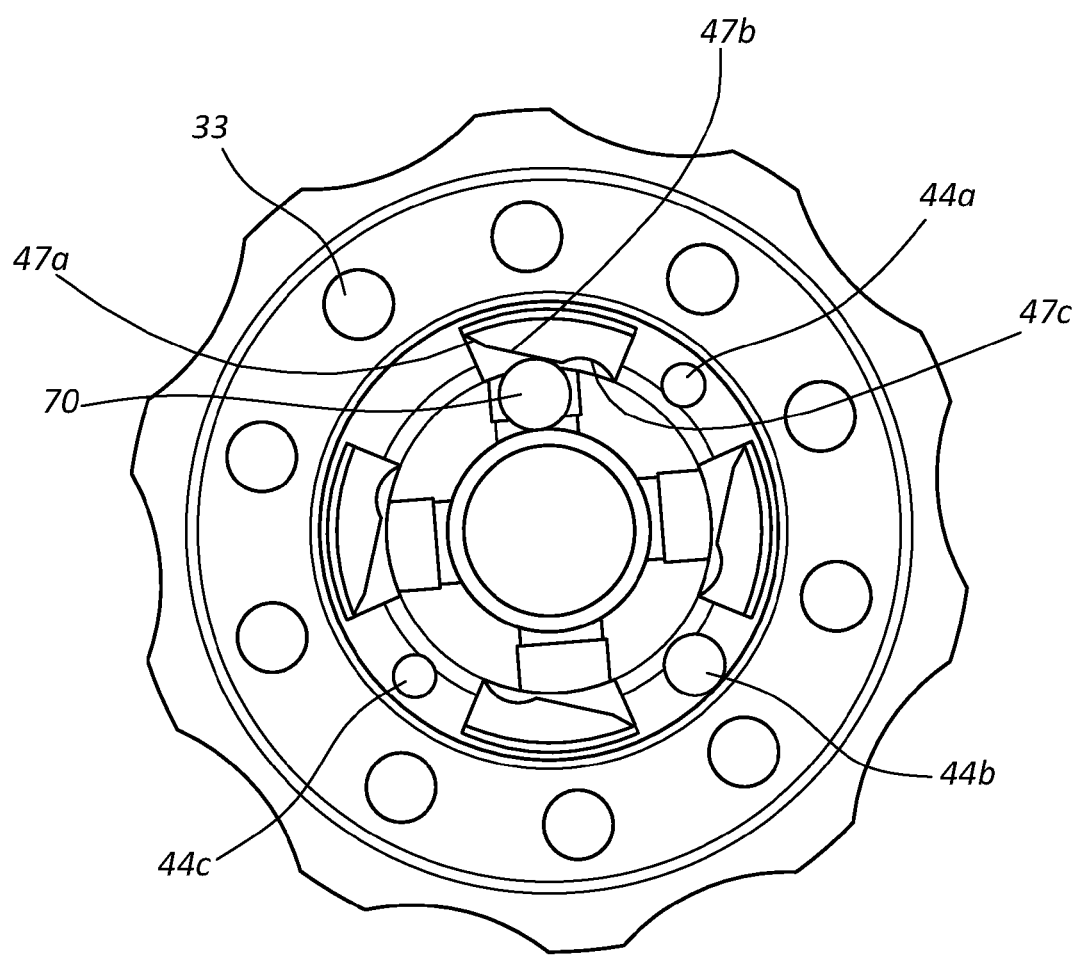
FIG. 8b illustrates an exemplary secured instrument adapter mechanism in its semi-engaged position.
Figure 8C:
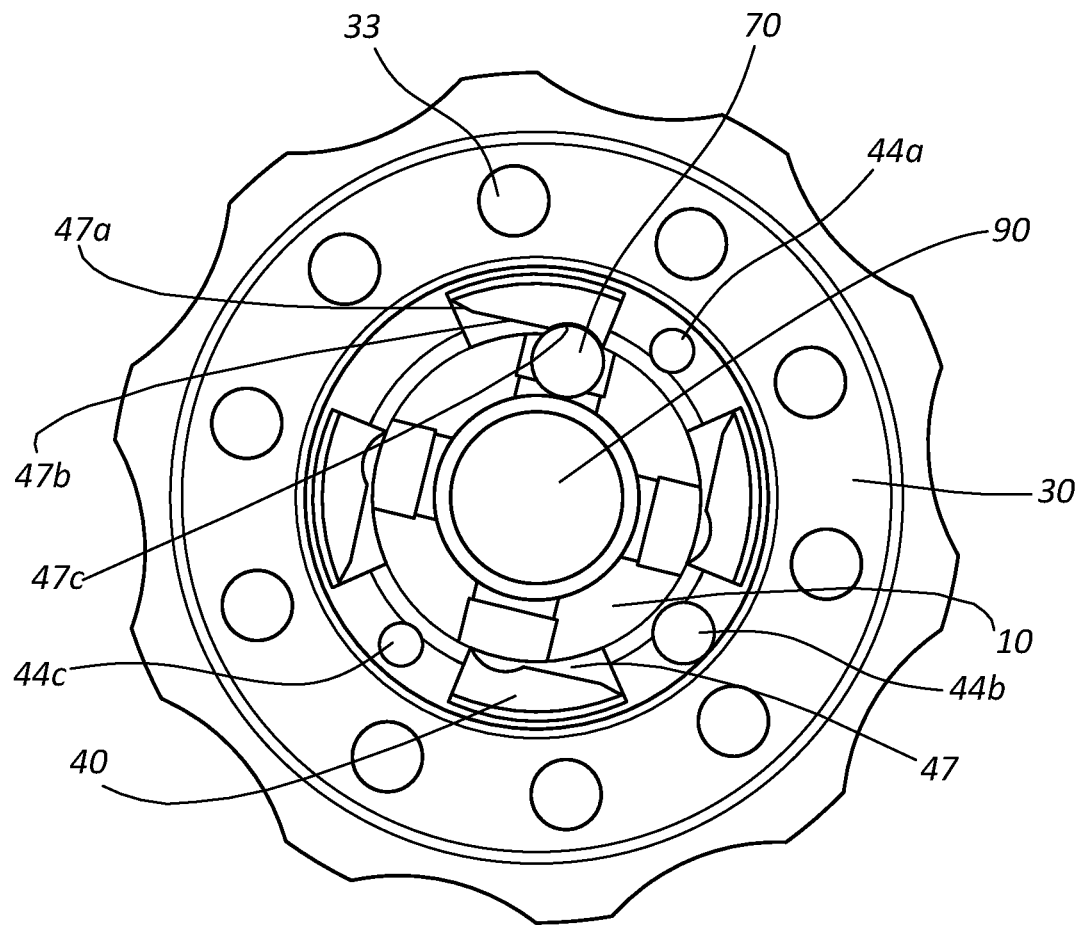
FIG. 8c illustrates an exemplary secured instrument adapter mechanism in its locked position.

FIGS. 8a, 8b and 8c illustrate an exemplary adapter's 100 securing mechanism.

FIG. 8a shows highly secure instrument adapter 100 at rest. Locking ball bearing 70 is in one of apertures 44, which are halfway between fingers 40. Locking ball bearing 70 is freely rotatable in aperture 44. As rotating collar 30 is rotated relative to instrument shaft 90 in a clockwise direction locking ball bearing 70 begins to be tightened between finger 40 and instrument shaft 90.

Because finger 40 is flexibly connected to rotating collar 30 at spacer structure 39 (not shown), finger 40 begins to flex outward from instrument shaft 90 as locking ball bearing 70 moves from lead-in surface portion 47a through ramp surface portion 47b, as illustrated in FIG. 8a. As rotating collar 30 is rotated, the amount of force required to rotate rotating collar 30 increases.

Once locking ball bearing 70 reaches locking engagement 47c, the final change of radius along contoured inner surface 47, locking ball bearing 70 locks into locking aperture 18 between instrument shaft 90 and finger 40, as illustrated in FIG. 8c.

In the exemplary embodiments shown, instrument shaft 90 has groove 93 (not shown) around its circumference and aligned with locking ball bearing 70 when inserted into highly secure instrument adapter 100. When in the locked position, as illustrated in FIG. 8c, locking ball bearing 70 pushes inward on instrument shaft 90, and is locked in groove 93 (not shown), thereby preventing instrument shaft 90 from being pulled outward from handle 80 (not shown).

To release instrument shaft 90, rotatable rotating collar 30 is forcibly rotated counterclockwise relative to instrument shaft 90, returning securing mechanism to its resting, or unlocked, position as illustrated in FIG. 8a. The flexibility provided by spacer structure 39 (not shown), which flexibly connects fingers 40 to rotating collar 30, allows a user to force locking ball bearing 70 out of locking engagement 47c to release instrument shaft 90.

The flexibility of spacer structure 39, and the rotating design of highly secure instrument adapter 100, also makes the locking functions impact-proof. For example, bumping instrument shaft 90 in any direction will not shake or move locking ball bearing 70 from the locked position, but may cause locking ball bearing 70 to flex finger 40 relative to instrument shaft 90, while locking ball bearing 70 remains in its locked position (engaging locking engagement 47c).

As illustrated in the exemplary embodiments shown in FIGS. 8a, 8b and 8c, it takes very little rotating to go from unlocked (FIG. 8a) to locked (FIG. 8c). The high radius of lead-in surface portion 47a of finger 40 causes locking ball bearing 70 to travel a greater distance over a smaller amount of rotation. Specifically, in the exemplary embodiment described, it is approximately 60 degrees from unlocked to locked position. In other words, it is 60 degrees from the center of locking ball bearing 70 at its resting position to the center of locking engagement 47c. However, in further exemplary embodiments, highly secure instrument adapter 100 may be designed with approximately 50-70 degrees of rotation required between the unlocked and locked positions.

The exemplary embodiment described in FIGS. 8a, 8b and 8c uses a single locking ball bearing 70. However, in further exemplary embodiments, four locking ball bearings 70 may be used to provide additional locking and securing stability for instrument shaft 90.

In the exemplary embodiments described, locking ball bearing 70 moves quickly over lead-in surface portion 47a, and then moves gradually over ramp surface portion 47b to locking engagement 47c. Both fast and gradual motion is needed because, if all fingers 40 only provided gradual motion, fingers 40 would need to be longer and there would not be space for four, or even two or more, fingers 40.

With too gradual of motion, it would also require over 60 degrees of rotation to get ball bearing 70 to engage locking engagement 47c. It is desirable to have as little rotation required as possible.

Figure 9:
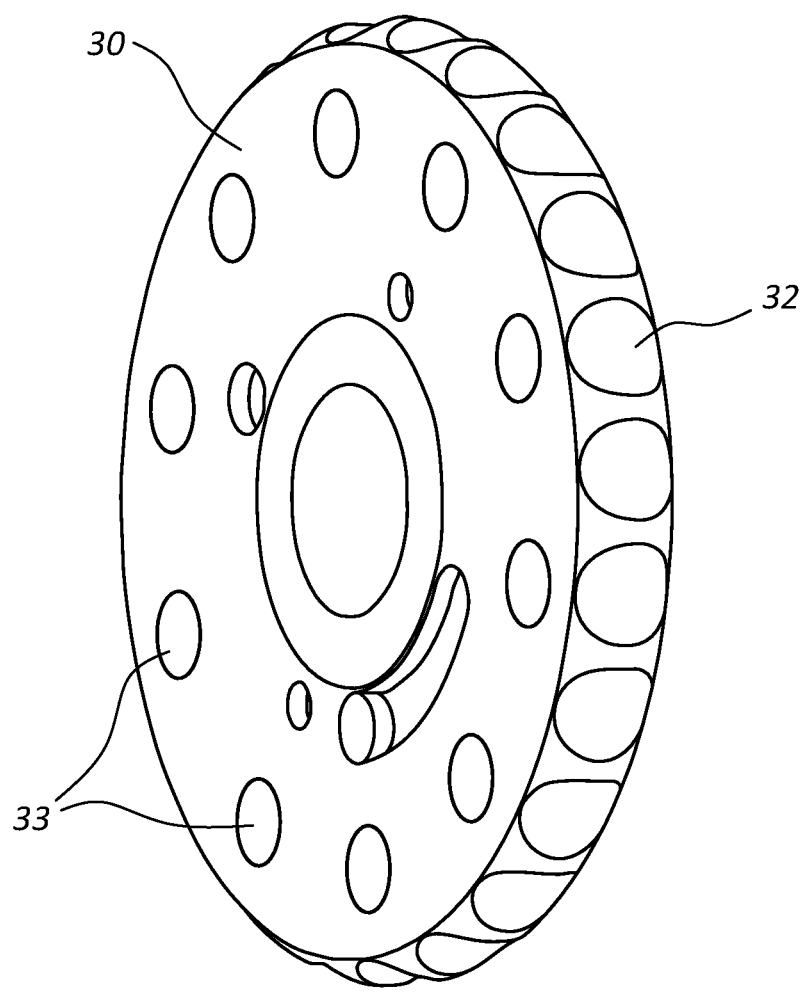
FIG. 9 illustrates an exemplary rotatable sixty degree rotating collar with a slot and pin control.

FIG. 9 is an exemplary embodiment of rotating collar 30 with slot and pin control.

What is claimed is:

1. A highly secure instrument adapter apparatus comprised of:
    an ergometric handle having an open handle cavity;
    a receiver having an internal threaded tubular body and a plurality of locking apertures;
    a rotating collar having a limited range of rotation comprising a plurality of fingers that project outward from a flattened surface on a spacer structure, and a plurality of circular apertures placed alternately between said plurality of fingers;
    an interconnected tube and a handle core;
    a stabilizing ball bearing assembly positioned inside said receiver;
    a locking ball bearing positioned inside said ergometric handle, said receiver and said rotating collar; and
    a thrust washer connected to said rotating collar,
    wherein each finger of said plurality of fingers is flexibly connected to said rotating collar by said spacer structure, and at least one of said plurality of fingers begins to flex outward from an instrument shaft as said locking ball bearing moves from a lead-in surface portion of one of said plurality of fingers through a ramp surface portion of said one of said plurality of fingers and to a locking engagement portion of said one of said plurality of fingers, increasing the amount of force required to rotate said rotating collar.

2. The apparatus of claim 1 wherein said rotating collar is configured to have a 50 to 70 degree range of rotation.

3. The apparatus of claim 1 wherein said stabilizing ball bearing assembly is comprised of at least one stabilizing ball bearing and at least one compression spring located inside at least one stabilizing aperture within said receiver.

4. The apparatus of claim 3 wherein said at least one compression spring engages said at least one stabilizing ball bearing and exerts a transverse force to said instrument shaft when said instrument shaft is inserted into a shaft cavity and said rotating collar is rotated.

5. The apparatus of claim 4 wherein said stabilizing ball bearing engages with a stabilizing contoured ball bearing groove in an inner surface of said rotating collar with a graduated variance in depth.

6. The apparatus of claim 5 wherein a maximum force is applied to said instrument shaft when said stabilizing ball bearing is in contact with a shallowest portion of said stabilizing contoured ball bearing groove.

7. The apparatus of claim 1 wherein said internal threaded tubular body has a flat outside end surface at a front of said receiver and a centralized shaft cavity creating a tubular passage completely through said receiver which is adapted to receive said instrument shaft.

8. The apparatus of claim 7 wherein said receiver also contains a plurality of locking apertures that are configured to engage said at least one locking ball bearing.

9. The apparatus of claim 8 wherein said receiver also contains at least one stabilizing aperture designed to house at least one stabilizing ball bearing and at least one compression spring.

10. The apparatus of claim 8 wherein said receiver also contains a plurality of centralizing chamfers designed to prevent axial movement of said instrument shaft.

11. The apparatus of claim 8 wherein said receiver terminates with an internally threaded end that fits an external thread on said interconnected tube.

12. The apparatus of claim 1 wherein said interconnected tube connects to said handle core within said handle cavity, and wherein said handle core fits into said handle cavity from a posterior end of said ergonomic handle.

13. The apparatus of claim 1 wherein said rotating collar contains radial frictional contours around its outside perimeter, an inward projection that terminates in a flattened surface and an internal receiver channel that runs through its length.

14. The apparatus of claim 13 wherein said receiver channel is configured with an internal diameter just larger than an external diameter of said receiver so that said receiver can fit securely inside said receiver channel.

15. The apparatus of claim 14 wherein said plurality of fingers each contain an outer surface that is curved at a consistent radius and a smooth inner surface that is also curved at a consistent radius.

16. The apparatus of claim 15 wherein the smooth inner surface of each said plurality of fingers transitions to a contoured inner surface that is tapered from a narrow end to a wider end.

17. The apparatus of claim 16 wherein the contoured inner surface of each said plurality of fingers consists of three distinct portions, each having a distinct critical angle or radius: said lead-in surface portion near the narrow end of the finger, said ramp surface portion in the middle that is flatter, and a locking engagement near the wider end of the finger, where said locking engagement is contoured to the radius of said locking ball bearing.

18. The apparatus of claim 17 wherein the lead-in surface portion is placed at angle of $\theta_A$ as measured from the centerline of the receiver channel, the ramp surface portion is placed at angle $\theta_B$ as measured from the centerline, and the locking engagement has a radius that corresponds to the radius of the locking ball bearing.

19. The apparatus of claim 17 wherein the different surface portions of the contoured inner surface on said plurality of fingers optimize the amount of rotation needed to lock and unlock said highly secure instrument adapter.

20. The apparatus of claim 1 wherein said locking ball bearing is in one of said apertures between said plurality of fingers in the rotating collar and is freely rotatable in said aperture when said highly secure instrument adapter is at rest.

21. The apparatus of claim 1 wherein said locking ball bearing moves along a contoured inner surface of of one of said plurality of fingers and begins to be tightened between one of said plurality of fingers and said instrument shaft as said rotating collar is rotated relative to said instrument shaft in a clockwise direction.

22. The apparatus of claim 1 wherein said locking ball bearing locks into one of said plurality of locking apertures in said receiver between said instrument shaft and at least one of said plurality of fingers once it reaches a locking engagement portion of a contoured inner surface of at least one of said plurality of fingers.

23. The apparatus of claim 1 wherein said instrument shaft has a groove around its circumference that is aligned with said locking ball bearing when inserted into said highly secure instrument adapter, so that said locking ball bearing pushes inward on said instrument shaft when in a locked position and is locked in said groove, thereby preventing said instrument shaft from being pulled outward from handle.

24. The apparatus of claim 1 wherein flexibility provided by said spacer structure allows a user to force said locking ball bearing out of locking engagement by forcibly rotating the rotating collar counterclockwise relative to said instrument shaft, thus releasing said instrument shaft and returning said highly secure instrument adapter apparatus to its resting, or unlocked, position.

25. The apparatus of claim 1 wherein flexibility of said spacer structure and rotatability of said highly secure instrument adapter makes the locking function impact-proof, as bumping said instrument shaft in any direction will not shake or move said locking ball bearing from the locked position, but may cause said locking ball bearing to flex one of said plurality of fingers relative to said instrument shaft while said locking ball bearing remains in its locked position.

* * * * *